US00PP08279P

United States Patent [19]

McGredy, IV

[11] Patent Number: Plant 8,279

[45] Date of Patent: Jun. 29, 1993

[54] HYBRID TEA ROSE PLANT NAMED MACGENEV

[75] Inventor: Sam McGredy, IV, Castor Bay, New Zealand

[73] Assignee: Roses by Fred Edmunds, Inc., Wilsonville, Oreg.

[21] Appl. No.: 812,140

[22] Filed: Dec. 18, 1991

[51] Int. Cl.[5] ..... A01H 5/00

[52] U.S. Cl. ..... Plt./18

[58] Field of Search ..... Plt./18, 19, 20

*Primary Examiner*—Howard J. Locker

*Attorney, Agent, or Firm*—Christie, Parker & Hale

[57] ABSTRACT

A new variety of hybrid tea rose plant having light pink flowers.

1 Drawing Sheet

SUMMARY OF THE INVENTION

The present invention relates to a new and distinct variety of rose plant of the hybrid tea rose class, which was originated by my crossing as seed parent the variety known as 'Harmonie' and as pollen parent the variety known as 'Auckland Metro'. The varietal denomination of this new rose is 'Macgenev'.

Among the novel characteristics possessed by this new variety which distinguishes it from its parents and all other varieties of which I am aware are its attractive light pink flowers attractively displayed against dark green foliage. The flowers are borne singly in a manner typical of hybrid tea varieties and on a plant suitable for growing outdoors in gardens.

Asexual reproduction by propagation by budding of the new variety as performed in Clackamas County, Oregon shows that the foregoing and other distinguishing characteristics come true to form and are established and transmitted through succeeding propagations. The new variety can be asexually propagated by budding, grafting, micropropagation and cuttings.

BRIEF DESCRIPTION OF ILLUSTRATION

The accompanying illustration shows typical specimens of the flowers and vegetative growth of the new variety depicted in color as nearly true as it is resonably possible to make the same in a color illustration of this character. Colors may vary depending upon growing conditions under different climate, soil, and cultivation conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart.

Parentage: Seedling.

*Seed parent.*—'Harmonie'.

*Pollen parent.*—'Auckland Metro'.

Class: Hybrid tea.

The following further horticultural observations were made of specimens grown outdoor in Clackamas County, Oregon in the month of September.

FLOWER

Blooming habit: Continuous.

A. Bud:

(1) *Size.*—Large.

(2) *Form.*—Ovoid.

(3) *Color.*—As sepals first divide, near 38A; when petals begin to unfurl, near 39D with 38A at edges.

(4) *Sepals.*—Barely longer than bud before reflexing; usually fancy, wooley inside — glabrous outside.

(5) *Peduncle.*—Length — medium-short. Aspect — straight. Strength — erect, thick as stem. Color — near 144A shaded 42A on sunny side.

B. Bloom:

(1) *Size.*—Average size when fully expanded — about 7 inches.

(2) *Borne.*—Singly, one to a stem, side buds rare.

(3) *Form.*—Spiral, imbricate, high centered at first, outer petals reflex to points others loosely roll under then become ruffled at maturity; petaloids and stamens evident in open bloom.

(4) *Petalage.*—Number of petals under normal conditions — about 25 to 30.

(5) *Color.*—After sepals fall and petals unfurl, inner petals at flower center (top surface) tends to near 39D to 49D and C. Outer petals (top surface) near 39D to 49D to C with deeper tone occasionally seen at petal edge. Reverse surface of outer petals approaches near 37D; reverse of other petals generally similar to top surface. Petal color near point of petal attached is near 10B. General tonality from a distance is attractive light pink with some darkening as blooms age (near 49B).

C. Petals:

(1) *Texture.*—Thick, firm, excellent substance.

(2) *Appearance.*—Inside and outside satiny.

(3) *Form.*—Deltoid, longer than wide.

(4) *Arrangement.*—Regularly arranged, imbricated.

(5) *Petaloids in center.*—Few.

(6) *Persistence.*—Drop off cleanly.

(7) *Fragrance.*—Intense old rose scent.

(8) *Lasting quality.*—Long lasting on plant and after cutting.

REPRODUCTIVE ORGANS

A. Stamens, filaments and anthers:

*Arrangement and color.*—Regularly arranged around styles, outer filaments longer than inner.
*Color.*—near 10B.

B. Pollen:
*Color.*—near 20A.

C. Styles: Few, uneven, contorted, color near 39B.

D. Stigmas: Near 10B.

E. Hips: Oval, medium size, 1-inch long × ⅝-inch wide, urn-shaped, near 144C when mature; few seeds barely protrude.

PLANT

A. Form: Upright.

B. Growth: Vigorous, free branching.
*Height attained.*—about 5 feet by September.

C. Foliage: Usually compound 5 leaflets.
(1) *Size.*—Medium.
(2) *Quantity.*—Abundant, short internodes.
(3) *Color.*—New foliage: Upper side — near 187A. Underside — near 187A. Old foliage: Upper side — near 139A. Underside — near 139C.
(4) *Shape.*—Long, oval, acuminate.
(5) *Texture.*—Upper side is shiny; underside is matte.
(6) *Edge.*—Lightly serrate.
(7) *Serration.*—Simple.

(8) *Leaf stem.*—Color — near 139B; underside near 139C.
(9) *Stipules.*—Short, lightly bearded.
(10) *Resistance to disease.*—Blackspot — above average. Mildew — excellent. Rust — excellent.

D. Wood:
(1) *New wood.*—Color — near 144B. Bark — smooth, shiny, few thorns, no prickles.
(2) *Old wood.*—Color — near 144A. Bark — smooth.

E. Thorns:
*Quantity (main stalk).*—Few.
*On laterals from stalk.*—Few.
*Form.*—Long pointed — slight recurve.
*Length.*—Short, usually 5/16-inch or less small.
*Color.*—Near 153B to 174B at base.
*Position.*—Irregular, scattered.
*Prickles.*—None.

F. Winter hardiness; Needs protection from extreme cold.

I claim:

1. A new and distinct variety of rose plant of the hybrid tea rose class, substantially as shown and described.

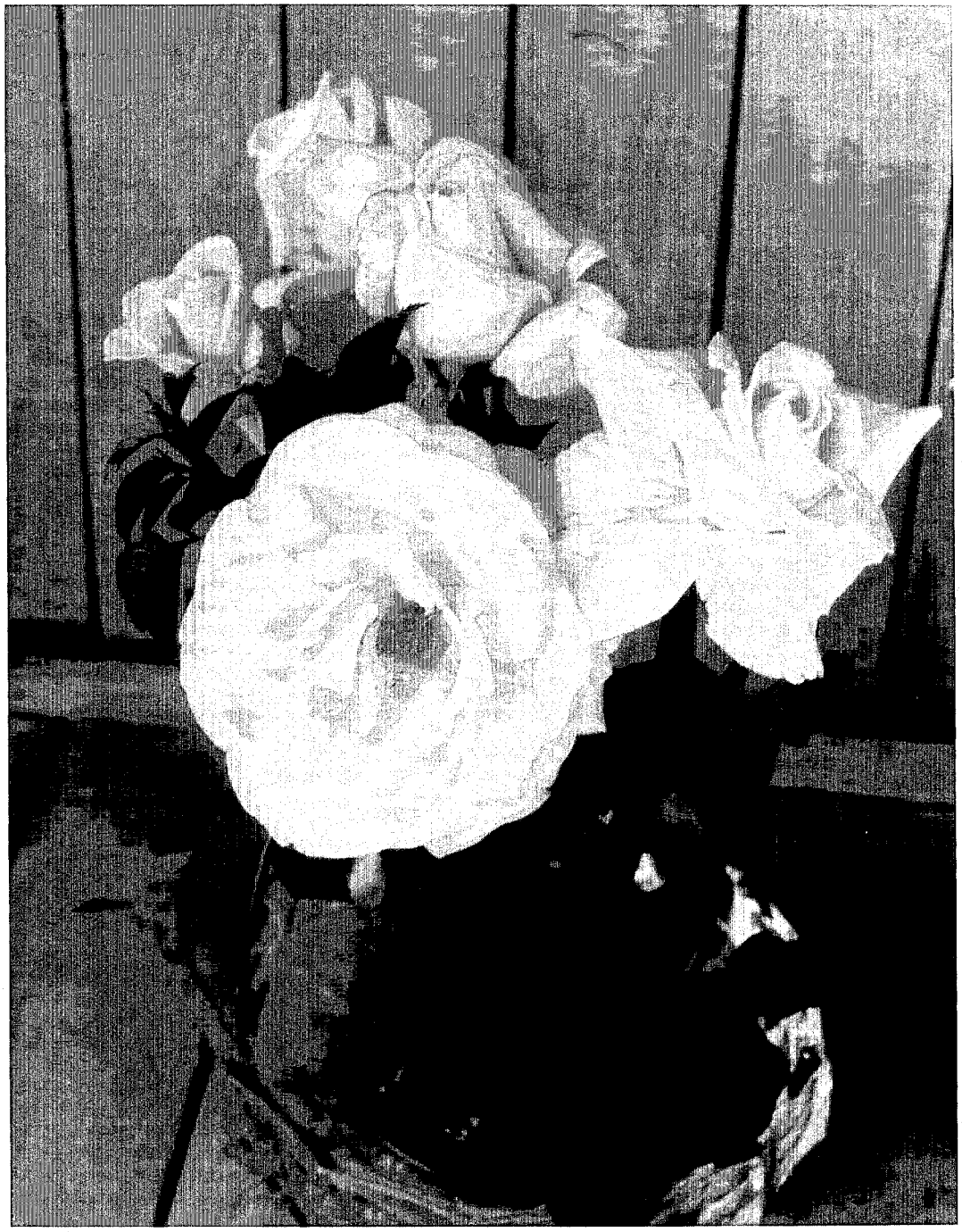

* * * * *